United States Patent [19]

Ziegler

[11] Patent Number: 4,594,237
[45] Date of Patent: Jun. 10, 1986

[54] METHOD FOR TESTING CHEMICAL AND BIOLOGICAL SUBSTANCES

[76] Inventor: Walter Ziegler, Wyhlenweg 18, 4126 Bettingen, Switzerland

[21] Appl. No.: 600,873

[22] Filed: Apr. 16, 1984

[51] Int. Cl.$^4$ ............................................. G01N 33/48
[52] U.S. Cl. ....................................................... 424/3
[58] Field of Search ............................................. 424/3

[56] References Cited

PUBLICATIONS

Chem. Absts., 9th Coll. Index, vol. 76–85 (1972–1976) p. 15069GS.

Primary Examiner—Sam Rosen
Attorney, Agent, or Firm—Armstrong, Nikaido, Marmelstein & Kubovcik

[57] ABSTRACT

The invention relates to a method for testing subtances for their cellulotoxic effect, which method involves treating tissues with the toxic substances to be examined or a mixture of toxic substances and sodium pyruvate so as to form plasma polypi and, the substance having been allowed time to act on the excised tissue treated, determining, by taking random samples, the content of plasma polypi qualitatively and quantitatively over the entire gastric mucosa using histological sections.

17 Claims, No Drawings

METHOD FOR TESTING CHEMICAL AND BIOLOGICAL SUBSTANCES

The invention relates to a method for testing chemical and biological substances, intended for or contained in medicaments, food, insecticides, pesticides, solvents and other everyday goods for their cellulotoxic effect, which method involves treating animal or human tissue with substances—in combination with sodium pyruvate, if required—so as to form plasma polypi (protrusions containing few cell organelles), which serve as a measure of the cellulotoxic effect, and, the substance having been allowed time to act on the excised tissue treated, determining the content of plasma polypi using histological sections.

BACKGROUND OF THE INVENTION

Test methods are generally means with which the functioning of human and animal organs is observed and changes perceived. Such methods involve chemical/biochemical analyses, continuous registrations and histological checks.

A special group of test methods are analysis methods, with the help of which nature and quantity of medicaments, stimulants, addictive substances and environmental poisons can be determined, e.g. blood alcohol determination, cardiac glycoside determination etc. Of the biological fluids to be investigated blood, blood plasma and urine are the most important, others including faeces, gland secretions such as saliva, gastric juice, bile, pancreatic juice, sweat, spinal fluid and exudates in the breast, stomach and joints. Examinations on organes are governed by the problem posed.

In view of the manifold requirements to be met by a diagnostic agent with regard to checking on the course of a disease, therapy checking and therapy control, and of the large amounts needed, repeated application is at first restricted to simple, inexpensive methods; with time, one will change over more and more to specific diagnostic agents for follow-up examinations.

Due to the continuous search for methods which are more convenient to handle and also more specific due to the fact that more and more examinations are carried out on the same object only once instead of several times and due to the non-toxicity of a substance category (in-vitro diagnosis) and not least for reasons of health politics, i.e. preventive medical checkups for the entire population, and the want of the individual to have preventive checkups, the importance of checking methods has been continuously increasing in recent times.

Functional diagnostic agents for checking on the physiological functioning of individual organs and organ systems play a special role among the checking methods. Related to these diagnostic agents are those that stimulate secretion by endocrine glands, thus providing a measure of the functional efficiency of, in particular, the stomach, pancreas etc.

Test methods for obtaining a functional diagnosis to assess how detrimental a substance is in respect of its cellulotoxic effect have already been studied by observing the formation of plasma polypi (PP).

In the publication Res. exp. Med. 171 (1977), pages 155 to 162, for example, experiments are described pertaining to the in-vitro production of plasma polypi (PP) found in human placentae after birth, in order to concentrate the polypi in one operation using reverse centrifugation and to obtain them as pure as possible.

In the publication "Archiv für Gynäkologie", 244 (1977), page 195 investigations are described concerning the commonness of acetylsalicylic acid in the placenta following parenteral administration to the mother during the birth, and in "Fortschr. med. 89 (1971)" pages 1159 to 1162, there is a report on the side-effects of salicylates on the human organism.

It is also already known that the poisoning of pregnant guinea pigs with mono-iodine-acetate or sodium fluoride as inhibitor of carbohydrate catabolism leads within a few minutes to significant morphological changes at the synctytiotrophoblast of the placenta. Besides swelling of the mitochondria, of the endoplasmic reticulum and of the Golgi's cisternae, as well as a nuclear pyknosis, a large number of plasma polypi occur (protrusions, 0.5 to 20 $\mu$m in size, with few organelles). In long-term experiments monitored for up to 10 days, these PP were found to lead to placenta infarcts. Histological examinations of human placentae which, following incubation in a shaker bath, had been cut into small strips also showed increased PP formation from the syncytiotrophoblast.

Increased formation of plasma polypi as symptom of pregnancy disorder is known from the publication "Archiv der Gynäkologie", 216 (1974), pages 175 to 176.

In experimental investigations carried out on animals to systematically research the causes of PP formation it was possible, by way of administering sodium fluoride (NaF) or mono-iodine-acetate to inhibit glucose catabolism, to obtain an increased, reproducible formation and pinching-off of cell protrusions in guinea-pig placentae.

The difficulty of assessing the results obtained by known determination methods is manifested particularly in the fact that many substances that have an effect on human or animal organisms, damage only becomes apparent after repeated application or prolonged periods of contact, e.g. softening agents in plastics, halogenated products, etc., going unnoticed to start with and then only being demonstrable through the use of complicated examination procedures. Since up to now it has not always been possible to demonstrate toxic effects simply and quickly with histological specimens, one was forced to carry out systematic series of tests on laboratory animals, which were expensive and time consuming.

The pinching-off of cell protrusions as a result of the effect of toxic substances and mechanical lesions, is a feature of all animal and human tissues, independent of the sex, e.g. tested on cell cultures of blood strain cells, hepatocytes, fibroblasts etc.

This result does not only apply to the syncytiotrophoblast, but also to anucleate erythrocytes. In the syncytiotrophoblast, which causes the exchange of blood gases of any one of substrates and the metabolic end products between mother and foetus, the cellular membrane is catabolized very quickly. Therefore, most tissues are ruled out for quantitatively registering of cell protrusions, because the PPs cannot be extracted quantitatively from the tissue in its entirety. For quantitatively registering PPs a comparatively large and accessible tissue surface is therefore required as is present, e.g. in the case of the placenta (see DE-PS No. 28 10 425). Registration carried out on the placenta employing said known method, however, was only applicable after the placenta had been completely rinsed off of blood and by determination of the PPs by way of reversed centrifugation, which was very time-consuming and necessitated fully developed animal and human placentae. This applies also to the possibility of observing the effect of toxic substances on individual villi of human placentae, in particular with regard to the period of formation and size of the PPs.

The present invention has the object of providing a test method with which toxic or undesirable side-effects of known and of new substances can be determined more quickly and more reliably than previously, and easily demonstrated.

Subject matter of invention is accordingly a method for testing chemical and biological substances intended for or contained in medicaments, food, insecticides, pesticides, solvents and other everyday goods for their cellulotoxic effect, which method involves treating animal or human tissue with the substances in question—in combination with sodium pyruvate, if required—so as to form plasma polypi (protrusions containing few cell organelles), which serve as a measure of the cellulotoxic effect, and, the substances having been allowed time to act on the excised tissue treated, determining the content of plasma polypi, characterized in that, by taking random samples, in the excised tissue the plasma polypi (PP) are determined qualitatively and over the entire excised gastric mucosa quantitatively using histological sections.

Most medicaments, substances needed every day and food first of all enter the stomach, where they remain for varying length of time. If the administered substances contain toxic substances the length of time and form of administration is demonstrable in a well defined and reproducible form.

The present invention is accordingly based on recognition of the fact that the formation of plasma polypi is a generally useful and reliable indicator of a certain type of cellulotoxic effect attributable to the test substance in question.

The test method according to the invention is of manifold application for determining whether the substance being tested is harmful to human or animal organs. In order to test the toxic effect in relation to the dose, use is made of a sex-independent tissue, namely the gastric mucosa.

The method used in the present invention for determining the content of plasma polypi on the gastric mucosa can be carried out in every industrial company or government laboratory.

Contrary to the conventional methods used for plasma polypi determination, for example at the placenta, the pinched-off plasma polypi formed on the large surface of the gastric mucosa pass directly into the lumen of the stomach free of foreign particles, i.e. free of blood and other tissue particles and can be extracted from the lumen of the stomach by removing and preparing the entire gastric tissue using standardized cuttings at the cardia and pylorus. Such extraction of PPs which are free of foreign particles is surprising and cannot be inferred from the prior art. Moreover, this method represents a great methodical adavance both with respect to its handling and the possibility of early diagnosis of damaging effects.

Contrary to the conventional test procedures, the method according to the invention represents an easy way of providing a quantitative measure of any cellulotoxic effect. The new method has the added advantage that gradual cellulotoxic effects of a substance, which up to now could only be histologically qualitatively detected after a long duration of action and delay, can now be determined with a good degree of reliability quantitatively and very quickly.

By conducting tests on the gastric mucosa it is easy to quantitatively determine the damage by counting the plasma polypi. In addition to this, the method of the invention makes it possible to determine the number of plasma polypi as a function of dose and duration of action.

It is thus possible, using simple histological sections, to determine—as a function of time—e.g. the damage done by acetyl salicylic acid also in the lower layers of cells. This allows one, in cases of repeated administration or raised individual doses, to observe all the stages of the damage, from simple lesions of the mucosa, ulceration and finally bleeding, since repeated administration or an overdose cause damage to the vascular endothelium as well.

By detecting and evaluating the PP one is able to make dose-dependent checks at intervals for possible damage or undesirable side-effects which any one substance may cause. This was up till now not possible.

Counting and determination of the size distribution are conducted microscopically, anything which is particularly unusual as regards shape or contents being photographed.

PP formation on the gastric mucosa occurs on individual cells that exhibit a relatively uniform size distribution of 1.0 to 3.0 $\mu$m diameter. Quantitative information on the toxic effect of a substance can be obtained within 1 day using the method of the present invention.

In the method according to the invention guinea pigs, hamsters, rats, mice, dogs, cats, pigs and monkeys are used as experimental animals, the substance to be tested, e.g. acetyl salicylic acid, pyridoxal phosphate, pyridoxal, formaldehyde, mono-iodine-acetate or the mixture to be tested comprising toxic substance and sodium pyruvate, being administered intravenously, intraperitoneally or intramuscularly or perorally.

With regard to the cellulotoxic effect, these animals react in a similar way to humans.

For closer details of the invention, attention is drawn to the test examples.

A positive test is proof of a toxic substance with increased PP formation on the gastric mucosa. Here, it has to be contemplated, for example, withdrawing the toxic substance from the market or combining it with another substance compensating for the cellulotoxic effect of said first toxic substance. Examples of such protective substances include: Na pyruvate, Na lactate, methylglyoxale, alanine, serine, glutamic acid, glutamine, aspartic acid, asparagine, 2-oxodicarboxylic acids and 2-oxotricarboxylic acids.

PP formation in the gastric mucosa of the rat occurs primarily at the surface layers of cells of the gastric mucosa. The plasma polypi are shed directly into the lumen of the stomach.

The PPs measure 1 to 5 $\mu$m, especially 1 to 2 $\mu$m, in diameter. PPs measuring 3 to 5 $\mu$m are the exception and account for only 3 to 5% of the total number.

Following administration of test substances such as acetyl salicylic acid (ASS) one can observe, depending on the length of time the substance remains in the stomach, when deeper layers of the gastric mucosa are affected and what effect the test substance has on vascular endothelium, i.e. whether bleeding occurs. The blood passes together with the PPs into the lumen of the stomach.

TEST EXAMPLES

PP formation, concentration and numbers thereof were determined using groups of 5 rats, each weighing 140 to 160 g, on average 150 g, and the number of PPs per 1 g stomach (empty) calculated.

The animals had not received any food for 15–17 hours prior to the test. The test substances were administered via a stomach tube, having first been dissolved in Krebs-Ringer solution (KRL) or in a. bidest. The pH-value of the solution administered was 7.0 to 7.2. The length of time for which the administered volume remains in the stomach depends in part on the properties of the test substance. It is shorter after administration of a.bidest, NaHCO₃, sodium lactate, but also after administration of nicotinic amide it is considerably shorter as compared to ASS, pyridoxol etc. The time which elapses until removal of the stomachs of a group was about 20 min up to a maximum of 30 minutes. The pinched-off PPs are registered as a function of dose.

The experiments showed that simultaneous administration of sodium pyruvate resulted in the gastric mucosa being protected, this being demonstrated by the reduced numbers of PPs.

The occurrence of lesions, ulcerations and bleeding can be suppressed to a large extent if e.g. 2 millimol Na pyruvate are added per millimol ASS.

5 animal experiments—combined to form one series—were performed, whereby in 40 min the stomachs being prepared as follows:

1. Each rat was administered, in non-narcotized state, a volume of 4.5 ml of the test substance (dissolved in KRL or a. bidest.) by means of a stomach tube.
2. Following a period of action of some 15 to 20 minutes, 40 to 45 mg Nembutal were administered intraperitoneally; 2 or 3 minutes were allowed to elapse, and the stomach then removed within a further 5 minutes.
3. The stomach was cut open, the contents collected and examined for PPs. The empty stomach itself was placed in an oxygenated Krebs-Ringer solution with the addition of glucose.
4. All 5 stomachs were homogenized, at high speed, three times; the homogenate was poured through a fine-meshed sieve through which 20 ml KRL were subsequently poured, so that one had an end volume of 80 ml.
5. The volumes from steps 3 and 4 were mixed with 8 ml of a 7% solution of a saccharose and epichloridrin copolymer, which sinks, and then centrifuged at 2000 revolutions for 20 minutes in a swing-tube rotor.
6. The layer, containing the PPs, is again centrifuged for 60 min at 13000 revolutions/min in the fixed-angle rotor (ultra centrifuge). The liquid was thrown away and the sediment processed further.
7. The sediment was then subjected to a reverse centrifugation in an ultracentrifuge at 25000 revs for 45 minutes.
8. The PPs from the reverse centrifugation, which had been collected in a bore, were introduced into 50 μl KRL.
9. A phase contrast microscope was employed to count the PPs of stage 8 a preparation of 3 μl being used in each case. 10 fields are counted with the raster objective, with added photographic checks. The values given in the table are derived in each case from 3 preparations of a sample of 5 rat stomachs, or from the evaluation of 30 fields.

$$\frac{\text{Average value per field} \times \text{conversion factor per field} \times 16.6}{6} = $$

number of PPs per g stomach

The conversion factor for the $18 \times 18$ mm² area is 24.652.

The substances listed in the table were injected and then the number of plasma polypi determined either as average value per g rat stomach for one series of 5 animals, or as the average for several series each containing 5 animals.

TABLE

| No. | Substance | No. of PPs per 1 g rat stomach | | No. of series (5 rats = 1 serie) |
|---|---|---|---|---|
| 1. | 4.5 ml a.bidest | about | 238.000 | 6 |
| 2. | 4.5 ml a.bidest with 1.33 mmol NaHCO₃ | | 333.700 | 4 |
| 3. | 4.5 ml a.bidest with 2.0 mmol Na—lactate | | 344.00 | 4 |
| 4. | 4.5 ml a.bidest with 0.5 mmol Na pyruvate | about | 220.000 | 1 |
| 5. | 4.5 ml a.bidest with 0.8 mmol pyridoxole | | 583.000 | 1 |
| 6. | 4.5 ml a.bidest with 2.1 mmol pyridoxole | | 1.039.000 | 1 |
| 7. | 4.5 ml a.bidest with 0.25 mmol ASS* | | 610.700 | 3 |
| 8. | 4.5 ml a.bidest with 0.5 mmol ASS* | | 728.000 | 3 |
| 9. | 4.5 ml a.bidest with 0.25 mmol ASS* and 0.5 mmol Na pyruvate | | 358.00 | 2 |
| 10. | 4.5 ml a.bides with 0.5 mmol ASS* and 1.0 mmol Na pyruvate | | 460.000 | 2 |

*ASS = acetyl salicylic acid

The PP formation starts off after a short period of reaction—depending on the structure of the test substance in question—and occurs primarily during the first 30 min. During the subsequent 90 min the PP formation decreases constantly and generally stops after 2 h. The period of action of the test substance is about 3 min to 90 min, the period during which PP formation reaches a maximum being a function of the test substance in question. The results in the table show that administration of sodium pyruvate does not result in an increased nunber of PPs as compared to the blank test (4.5 ml a.bidest). If sodium pyruvate and ASS are administered simultaneously, a considerable reduction in PP formation induced by the toxic substance ASS is attained.

I claim:

1. A method for testing chemical and biological substances for cellulotoxic effects, comprising:
    (a) treating animal tissue with the substance to be tested so as to form plasma polypi, which serve as a measure of the cellulotoxic effect,
    (b) allowing the substance to have time to act on the tissue treated,
    (c) excising the tissue treated and taking random samples from the excised tissue to determine the content of plasma polypi qualitatively and quantitatively over the entire excised tissue using histological sections, and
    (d) comparing the number of plasma polypi produced to a comparative standard of cellulotoxic effect.

2. The method according to claim 1 wherein the animal tissue is human tissue.

3. The method according to claim 1 wherein the animal tissue is gastric mucosa.

4. The method according to claim 3, wherein the entire gastric tissue associated with the gastric mucosa is removed and prepared to determine the number of plasma polypi that are shed into the lumen of the stomach and formed from the gastric mucosa.

5. The method according to claim 1 wherein sodium pyruvate is combined with the substance to be tested.

6. The method according to claim 5, wherein the animal tissue is human tissue.

7. The method according to claim 5, wherein the animal tissue is gastric mucosa.

8. The method according to claim 7, wherein the entire gastric tissue associated with the gastric muscosa is removed and prepared to determine the number of plasma polypi that are shed into the lumen of the stomach and formed on the gastric mucosa.

9. The method according to claim 8, wherein plasma polypi that are shed, into the lumen of the stomach and plasma polypi that are formed from the gastric mucosa are counted in a liquid phase subsequent to the stomach having been homogenized.

10. The method according to claim 9, wherein the substance to be tested is allowed to act on the gastric mucosa for 3 to 90 min.

11. The method according to claim 10, wherein the period of action is 15 to 30 min.

12. The method according to claim 6, wherein acetyl salicylic acid as a cellulotoxic substance and sodium pyruvate as a protective substance are introduced into the stomach in a molar ration of 1 to 2.

13. The method according to claim 4, wherein plasma polypi that are shed, into the lumen of the stomach and plasma polypi that are formed from the gastric mucosa are counted in a liquid phase subsequent to the stomach having been homogenized.

14. The method according to claim 13, wherein the substance to be tested is allowed to act on the gastric mucosa for 3 to 90 min.

15. The method according to claim 14, wherein the period of action is 15 to 30 min.

16. The method according to claim 3, wherein acetyl salicylic acid as a cellulotoxic substance and sodium pyruvate as a protective substance are introduced into the stomach in a molar ratio of 1 to 2.

17. The method according to claim 1, wherein at least one of, pyridoxalphosphate, pyridoxal, formaldehyde and monoiodine acetate is used as a cellulotoxic substance.

* * * * *